United States Patent

Kiss et al.

[11] Patent Number: 6,049,011
[45] Date of Patent: Apr. 11, 2000

[54] HYDROFORMYLATION PROCESS

[75] Inventors: Gabor Kiss, Hampton; Michael G Matturro, Lambertville; Harry William Deckman, Clinton; Frank Hershkowitz, Liberty Corner, all of N.J.; David R. Lumgair, Jr., Kingwood, Tex.; Gary F Janda; Daniel N King, both of Houston, Tex.

[73] Assignee: Exxon Chemical Patents Inc., Houston, Tex.

[21] Appl. No.: 08/875,157

[22] PCT Filed: Jan. 17, 1996

[86] PCT No.: PCT/EP96/00163

§ 371 Date: Oct. 15, 1997

§ 102(e) Date: Oct. 15, 1997

[87] PCT Pub. No.: WO96/22265

PCT Pub. Date: Jul. 25, 1996

[30] Foreign Application Priority Data

Jan. 18, 1995 [EP] European Pat. Off. ............... 95300301

[51] Int. Cl.[7] .................................................. C07C 45/00
[52] U.S. Cl. .................... 568/451; 568/454; 568/878; 568/882; 568/883; 560/233; 560/247
[58] Field of Search .................... 568/454, 451, 568/882, 883, 878; 560/233, 247

[56] References Cited

U.S. PATENT DOCUMENTS

| | | | |
|---|---|---|---|
| 3,527,809 | 9/1970 | Pruett et al. | 260/604 |
| 3,917,661 | 11/1975 | Pruett et al. | 260/410.9 |
| 4,148,830 | 4/1979 | Pruett et al. | 260/604 |
| 4,248,802 | 2/1981 | Kuntz | 568/454 |
| 4,287,369 | 9/1981 | Harris et al. | 568/454 |
| 4,287,370 | 9/1981 | Harris et al. | 568/454 |
| 4,322,564 | 3/1982 | Tsunoda et al. | 568/454 |
| 4,479,012 | 10/1984 | Fischer et al. | 568/454 |
| 4,523,036 | 6/1985 | Cornils et al. | 568/454 |
| 4,533,757 | 8/1985 | Kummer et al. | 568/454 |
| 4,577,043 | 3/1986 | Kalbfell et al. | 568/454 |
| 4,593,127 | 6/1986 | Bunning et al. | 568/454 |
| 4,742,178 | 5/1988 | Nelson et al. | 568/454 |
| 4,769,984 | 9/1988 | Raasch et al. | 57/407 |
| 4,808,756 | 2/1989 | Tokitoh et al. | 568/454 |
| 4,885,401 | 12/1989 | Billig et al. | 568/454 |
| 5,105,018 | 4/1992 | Miyazawa et al. | 568/453 |
| 5,312,951 | 5/1994 | Herrmann et al. | 558/45 |
| 5,347,045 | 9/1994 | Hermann et al. | 562/35 |
| 5,367,106 | 11/1994 | Unruh et al. | 568/453 |

FOREIGN PATENT DOCUMENTS

| | | |
|---|---|---|
| 3985 | 9/1979 | European Pat. Off. . |
| 0225143 | 6/1987 | European Pat. Off. . |
| 2249061 | 6/1975 | France . |
| 3220858 | 12/1983 | Germany . |
| 1387657 | 3/1975 | United Kingdom . |

OTHER PUBLICATIONS

Perry, et al., "Perry's Chemical Engineers' Handbook", pp. 23–1 to 23–9, 23–15 to 23–26, 23–39 to 23–52, (7th edition), 1997.

"New Syntheses w/Carbon Monoxide", by Ed. J. Falbe, Springer Verlag, New York, 1980, especially the chapter-"Hydroformylation, Oxo Synthesis, Roelen Reaction," by B. Cornils.

"High yield synthesis of propanal from methane and air", by Green et al., Catalysis Letters, 13, (1992), pp. 341 to 347.

Yin et al., "Study of Supported Liquid Phase Catalysts for Hydroformylation of Olefins contained in FCC Dry Gas", pp. 614–620, vol. 2, Proceedings of the International Conference on Petroleum Refining and Petrochemical Processing, Sep. 11–15, 1991, Beijing, China.

*Primary Examiner*—Shailendra Kumar
*Assistant Examiner*—Sreeni Padmanabhan
*Attorney, Agent, or Firm*—Douglas J. Collins

[57] ABSTRACT

A dilute ethylene stream, e.g., one produced by steam cracking, is oxonated to yield propanal, without the need to separate other lower hydrocarbons.

38 Claims, 1 Drawing Sheet

HYDROFORMYLATION PROCESS

This is the U.S. National stage Application of PCT/EP96/00163 filed Jan. 17, 1996 now WO96/22265 Published Jul. 25, 1996.

FIELD OF THE INVENTION

This invention relates to a process for hydroformylation of a dilute ethylene-containing feedstream.

BACKGROUND OF THE INVENTION

It has been recognized that in principle the lower unsaturated hydrocarbon component in certain hydrocarbon streams is a valuable source for higher organic molecules. Such higher organic molecules may be reached, for example, by treatment, for example hydroformylation, of unsaturated hydrocarbons, in particular those containing two carbon atoms, the unsaturated hydrocarbons being obtainable, for example, by pyrolysis of hydrocarbons, more especially their pyrolysis in the presence of steam to form a light olefin-containing mixture, or pyrolysis of methane in appropriate conditions, as described in U.S. patent application Ser. No. 375,324 of Jan. 18th, 1995, and a corresponding PCT application entitled "Direct Hydroformylation of a Multi-Component Synthesis Gas Containing Carbon Monoxide, Hydrogen, Ethylene and Acetylene", applicants Gabor Kiss et al., assigned to Exxon Research & Engineering Company, filed simultaneously with the present application, and whose entire disclosures are incorporated by reference herein.

DESCRIPTION OF THE RELATED ART

In European Patent Application No. 95.300 301.9 of Jan. 18th, 1995, and a corresponding PCT application entitled "Organic Compounds and Processes for their Manufacture", filed by the present applicants simultaneously with the present application, and whose entire disclosures are incorporated by reference herein, there are disclosed processes for the manufacture of aldehydes, primarily those containing 9 carbon atoms, and their derivatives, optionally from an unsaturated hydrocarbon containing two carbon atoms, which is in turn optionally obtained by appropriate treatment of natural gas.

In view of the desirability of being able to make the best possible economic use of the various dilute olefin sources, e.g., natural gas, stream cracking and other hydrocarbon sources, becoming available around the world, there remains a need for a hydroformylation procedure sufficiently flexible to use ethylene-containing feedstocks of a variety of compositions.

In DE-OS 2354217 (BASF AG), there is disclosed a process in which an ethylene-containing feedstream is hydroformylated. In this process, a mixture of gases resulting from thermal cracking of oil is treated to abstract pure ethylene, acetylene or butadiene, and a feedstock of the residual gases, being primarily $C_2$ to $C_4$ olefins, carbon monoxide and hydrogen, is contacted with a rhodium-based catalyst under hydroformylation conditions. In the examples, the hydrocarbons are methane and ethylene only, and the ethylene represents from 76 to 99% volume percent of the hydrocarbon content.

In Vol. 2 of the Proceedings of INTERPEC 91, at pp 614 to 620, Yin et al describe hydroformylation of a feedstream, resulting from fluid bed catalytic cracking, using syngas in the presence of a supported liquid phase rhodium-based catalyst. The ethylene content of the feedstream, based on total hydrocarbon content, is below 30 volume percent. The hydrocarbon content of the stream is about 50% by volume, the remainder being hydrogen, about 30%, and nitrogen, about 19%.

In Catalysis Letters, 13, (1992), 341 to 347, Green et al describe the synthesis of propanal from methane and air by oxidative coupling of a portion of the methane to ethylene, partial oxidation of another portion of the methane to syngas, and hydroformylation of the ethylene-containing feedstream by the syngas. In a proposal to use natural gas as a methane source, ethane is cryogenically separated out of the natural gas before oxidative coupling. In an example, the ethylene content of the feedstream to hydroformylation is about 10 volume percent, based on the hydrocarbon content.

BRIEF SUMMARY OF THE INVENTION

The present invention provides a process for the hydroformylation of a hydrocarbon-containing feedstream which comprises contacting a feedstream containing from 27.5 to 75 percent by weight of ethylene, based on the total hydrocarbon content, and having a total olefin content of at most 80% by weight, also based on the total hydrocarbon content, with synthesis gas under hydroformylation conditions in the presence of a rhodium-containing catalyst and recovering a hydroformylation product.

DETAILED DESCRIPTION OF THE INVENTION

The term "feedstream source" is used herein to denote a dilute ethylene stream available from various chemical and refining processes exemplified below. Depending on its components, the feedstream source may or may not require treatment to render it acceptable as the feedstream to the hydroformylation process of the present invention. It is, however, as discussed below, an advantage of the present invention that the feedstream source may require minimal treatment to render it acceptable as the feedstream, also referred to below as the dilute ethylene feedstream.

Advantageously, the feedstream source is obtained by pyrolysis of hydrocarbons, for example steam cracking of ethane, and contains the major proportion of the product, i.e., is not merely the residual gases. The invention is, however, also applicable to other feedstream sources e.g., from other hydrocarbon cracking operations, the hydrocarbon being selected from light hydrocarbon gases e.g., ethane, through light liquid, e.g., naphtha, to heavy liquid hydrocarbons, e.g., vacuum gas oil, cracking being, for example, catalytic, thermal or steam cracking, or hydrocracking. The feedstream source may also result from the catalytic conversion of alcohols, for example methanol to ethylene, Fischer-Tropsch conversion, catalytic dehydrogenation of saturated hydrocarbons, (especially of ethane) or petroleum coking processes, or be the purge stream from a process using higher purity ethylene as feed, e.g., polymerization.

Although the feedstream source, from whatever origin, is treated before hydroformylation to remove catalyst poisons (e.g., sulphur-, nitrogen- and chlorine-containing compounds, and oxygen), if present, or reduce them to a level at which catalyst life is economically acceptable, it is an advantage of the process of the invention that this is the only pretreatment needed. Other species initially present in the feedstream source may accordingly be allowed to remain, thereby avoiding the need for, for example, cryogenic ($-100°$ C. to $-75°$ C.) separation normally employed in manufacture of high purity ethylene, or hydrogenation under severe conditions to remove the acetylene produced by pyrolysis.

Advantageously, the feedstream source before any treatment contains the following components, by weight of total hydrocarbon content:

| | |
|---|---|
| Methane | up to 30% |
| Acetylene | up to 2.0% |
| Ethylene | up to 65% |
| Ethane | up to 50% |
| Propene | up to 50% |
| Propane | up to 10% |
| $C_4^+$ | up to 95% |
| Polyunsaturates | up to 1.5% |

(As used herein, the term polyunsaturates includes compounds having two or more unsaturated carbon to carbon bonds, whether double or triple, and also compounds other than acetylene which contain one triple bond, e.g., propyne.)

Higher boiling components, especially $C_5^+$ hydrocarbons, may be removed from such a feedstream source as a desirable product, e.g., naphtha from fluid bed catalytic cracking, as a result of processing or to avoid further handling of by-products. For example, the tar formed from steam cracking of vacuum gas oil may be removed as an undesirable by-product in the primary fractionation of the process gas, while the $C_5^+$ component of the product from steam cracking of ethane may be removed during the quench and process gas compression stages immediately following cracking.

Intermediate boiling components ($C_3^+$) of a feedstream source may also be removed from the dilute olefin stream as a desired co-product or to avoid further handling of by-products. For example, propene may be removed from the process gas effluent of cracked naphtha for use as a chemical feedstock.

The desired concentration of ethylene for hydroformylation may be achieved using conventional separation processes, for example fractionation or absorption, to remove the higher boiling components. This, however, is not essential for the operation of the inventive process, and other typical components, e.g., hydrogen, nitrogen, carbon monoxide, water, methane, acetylene, ethane, propane, propene, and alkadienes may be present. Advantageously, the feedstream contains at most, 1% of, and is preferably substantially free from, $C_4^+$ components; advantageously, also the stream contains at most 2% of, acetylene, and advantageously the stream contains at most 10%, preferably at most 5%, of molecular nitrogen, and is most preferably substantially free from molecular nitrogen, the percentages being by weight. Advantageously, the total level of sulphur-, chlorine-and nitrogen-containing compounds is at most 1 wppm and preferably the feedstream is substantially free from such compounds. Further, the level of oxygen is at most 10 wppm and the stream is preferably substantially free from oxygen. Preferably, the acetylene content by mole of the feedstream is less than 1% of the ethylene content, and most preferably it is substantially acetylene-free.

The conventional processes for removal of catalyst poisons, for example, reactive separation (e.g., caustic wash), catalytic conversion (e.g., hydrogen) or fixed bed adsorption (e.g., ZnO) may be used to pretreat dilute ethylene feeds containing sulphur- or nitrogen-compounds, for example, hydrogen sulphide removal from refinery streams. Oxygen removal may be accomplished by fixed bed adsorption, for example reduced copper or chemical conversion, for example hydrogenation over a precious metal catalyst, for example palladium or platinum.

Advantageously, the dilute ethylene feedstream contains the following components, by weight of total hydrocarbon content:

| | |
|---|---|
| Methane | up to 30%, preferably 0.4 to 30% |
| Acetylene | up to 2.0%, preferably up to 1.5% |
| Ethylene | 27.5 to 75%, more advantageously 30 to 75%, preferably 30 to 60% and most preferably 45 to 60% |
| Ethane | up to 50%, preferably 0.1 to 40% |
| Propene | up to 50%, preferably 0.5 to 10% |
| Propane | up to 10%, preferably 0.1 to 5% |
| $C_4^+$ | up to 70%, preferably less than 1% |
| Polyunsaturates | up to 1.5% |

In addition, as indicated above, the dilute ethylene feedstream may contain nitrogen in limited quantities and hydrogen, for example up to 6%, by weight of the total feedstream. Advantageously the hydrocarbon content of the feedstream is at least 50%, more advantageously at least 80%, and preferably at least 90%, and most preferably at least 94%, by weight. The feed may also contain carbon monoxide, carbon dioxide, and water vapour.

As examples of suitable sources of feeds and their typical make-up, there may be mentioned the following:

A—Process Gas from Steam Cracking of Ethane

| Component | Approximate Wt. % |
|---|---|
| Hydrogen | 3.6 |
| Methane | 3.7 |
| Acetylene | 0.3 |
| Ethylene | 48 |
| Ethane | 40 |
| Polyunsaturates | 0.07 |
| Propene | 1.2 |
| Propane | 0.2 |
| $C_4^+$ | 3.0 |

B—Process Gas from Steam Cracking of Naphtha

| Component | Approximate Wt. % |
|---|---|
| Hydrogen | 1.0 |
| Methane | 16.0 |
| Acetylene | 0.6 |
| Ethylene | 33.0 |
| Ethane | 4.5 |
| Polyunsaturates | 0.8 |
| Propene | 16.8 |
| Propane | 0.5 |
| $C_4^+$ | 26.7 |

C—Light Gas from Fluidized Catalytic Cracking

| Component | Approximate Wt. % |
|---|---|
| Hydrogen | 0.4 |
| Methane | 33.6 |
| Ethylene | 30.0 |

| Component | Approximate Wt. % |
|---|---|
| Ethane | 31.4 |
| Propene | 4.6 |

D—Process Gas from Vacuum Gas Oil Cracking

| Component | Approximate Wt. % |
|---|---|
| Hydrogen | 0.5 |
| Methane | 10.3 |
| Acetylene | 0.2 |
| Ethylene | 19 |
| Ethane | 5 |
| Polyunsaturates | 0.5 |
| Propene | 13.5 |
| Propane | 0.6 |
| $C_4$'s | 8.4 |
| Tar | 11 |
| Other $C_5^+$ | 31 |

Although, as indicated above, the process of the invention does not require the removal of other typical components, the concentration of these components may, if desired, optionally be controlled using conventional processing steps. More specifically, acetylene and polyunsaturates, for example propadiene or butadiene may be controlled to a target level by chemical conversion, for example hydrogenation or extraction, for example absorption by acetone or water. The concentration of $C_3^+$ components, for example propene, propadiene or butadiene, may be further managed by fractionation, for example simple distillation.

As will be described in more detail below, in a preferred embodiment of the process, the feedstream source, advantageously a dilute ethylene stream resulting from steam cracking of ethane, is converted after quenching to an acceptable form for hydroformylation by being compressed, washed in an aqueous alkaline solution, then with water, and optionally dried. If desired, the resulting, preferably dry, feedstream may be hydrogenated, fractionated, and de-oxygenated before being hydroformylated. A typical resulting dilute ethylene feedstream has the following composition:

E—Dilute Ethylene Feedstream from Steam Cracking of Naphtha

| Component | Approximate Wt. % |
|---|---|
| Hydrogen | 3.7 |
| Methane | 3.8 |
| Acetylene | less than 500 ppm |
| Ethylene | 50 |
| Ethane | 42 |
| Polyunsaturates | less than 100 ppm |
| Propene | 0.2 |
| Propane | less than 0.2 |
| $C_4^+$ | 0.2 |
| Sulphur Compounds | less than 1 ppm |
| Oxygen | less than 10 ppm |
| Nitrogen Compounds | less than 1 ppm |
| Chlorine Compounds | less than 1 ppm |
| Water | less than 10 ppm |

F—Dilute Ethylena Feedstream from Steam Cracking of Naphtha and Refining

| Component | Approximate Wt. % |
|---|---|
| Hydrogen | 1.6 |
| Methane | 27.2 |
| Acetylene | 1.0 |
| Ethylene | 56 |
| Ethane | 7.7 |
| Polyunsaturates | 1.4 |
| Propene | 3.4 |
| Propane | 0.9 |
| $C_4^+$ | 0.8 |
| Sulphur Compounds | less than 1 ppm |
| Oxygen | less than 10 ppm |
| Nitrogen Compounds | less than 1 ppm |
| Chlorine Compounds | less than 1 ppm |
| Water | less than 10 pp |

As described in more detail in the above-identified co-pending U.S. and PCT applications, the literature contains many references to hydroformylation of pure ethylene with syngas; literature sources include "New Syntheses with Carbon Monoxide", Ed. J. Falbe, Springer Verlag, New York, 1980, especially the Chapter "Hydroformylation, Oxo Synthesis, Roelen Reaction" by B. Cornils; U.S. Pat. Nos. 3,527,809, 3,917,661 and 4,148,830, which describe an oil soluble phosphine-modified rhodium catalyst; and U.S. Pat. Nos. 4,742,178, 4,769,984 and 4,885,401, the disclosures of all these documents being incorporated herein by reference. According to the present invention, hydroformylation is advantageously carried out using as catalyst an oil-soluble rhodium complex comprising a low valence rhodium (Rh) complexed both with carbon monoxide and a triorganophosphorus compound. As triorganophosphorus compound there may be mentioned, for example, one or more oil-soluble triarylphosphines, trialkylphosphines, alkyl-diarylphosphines, aryl-dialkylphosphines, triorganophosphites, especially trialkylphosphites and triarylphosphites (in which list alkyl includes cycloalkyl), containing one or more phosphorus atoms per molecule capable of complexation with Rh by virtue of having a lone pair of electrons on the phosphorus. Instead of, or in addition to, such monodentate compounds, at least one bidentate phosphorus compound may be used as ligand. Triorganophosphorus ligands which are known to provide good catalytic activity in the hydroformylation of pure olefin feeds are suitable for use in the process of the present invention, their concentration preferably being such that (a) the molar P/Rh ratio is at least 2:1, (b) the total concentration of the coordinately active phosphorus is preferably at least 0.01 mol/l; and (c) the [P]/pco ratio maintained in the reactor is preferably at least 0.1 mmol/l/kPa, where [P] is the total concentration of the coordinately active phosphorus in the solution, and Pco is the partial pressure of carbon monoxide in the gas phase.

As examples of the ligands there may be mentioned trioctylphosphine, tricyclohexylphosphine, octyldiphenylphosphine, cyclohexyldiphenylphosphine, phenyldioctylphosphine, phenyldicyclohexylphosphine, triphenylphosphine, tri-p-tolylphosphine, trinaphthylphosphine, phenyl-dinaphthylphosphine, diphenylnaphthylphosphine, tri-(p-methoxyphenyl) phosphine, tri-(p-cyanophenyl)phosphine, tri-(p-nitrophenyl)phosphine, and p-N,N-dimethylaminophenyl (diphenyl)phosphine, trioctylphosphite or tri-p-tolylphosphite; as bidentate compound there may be mentioned diphos-bis(diphenylphosphino)ethane.

Advantageously, the Rh concentration in the reaction mixture is in the range from $1 \times 10^{-5}$ to $1 \times 10^{-2}$ moles/litre or, in effect, in the range from 1 to 1000 ppm, preferably 20 to 500 ppm, based on the total weight of the solution.

The catalyst is advantageously contacted with the feedstream in a solution in an oily solvent or a mixture of such solvents, for example aliphatic and aromatic hydrocarbons (e.g., heptanes, cyclohexane, toluene), esters (e.g., dioctyl phthalate), ethers, and polyethers (e.g., tetrahydrofuran, and tetraglyme), aldehydes (e.g., propanal, butanal) the condensation products of the oxo product aldehydes or the triorganophosphorus ligand itself (e.g., triphenylphosphine).

Alternatively, as described in U.S. Pat. Nos. 4,248,802, 4,808,756, 5,312,951 and 5,347,045, which are all incorporated herein by reference, the catalyst may contain a hydrophilic group and an aqueous medium may be used.

Rhodium may be introduced into the reactor either as a preformed catalyst, for example, a solution of hydridocarbonyl tris(triphenylphosphine) rhodium(I) or it may be formed in situ. If the catalyst is formed in situ, the Rh may be introduced as a precursor such as acetylacetonatodicarbonyl rhodium(I) $\{Rh(CO)_2(acac)\}$, rhodium oxide $\{Rh_2O_3\}$, rhodium carbonyls $\{Rh_4(CO)_{12}, Rh_6(CO)_{16}\}$, tris (acetylacetonato) rhodium(I), $\{Rh(acac)_3\}$, or a triaryl phosphine-substituted rhodium carbonyl $\{Rh(CO)_2(PAr_3)\}_2$, wherein Ar is an aryl group.

Hydroformylation is advantageously conducted at a temperature in the range from 40 to 200° C., more advantageously from 80 to 180° C., and preferably from 90 to 155° C.

The reaction is advantageously conducted at a low pressure, e.g., a pressure in the range of 0.05 to 50 MPa (absolute), and preferably in the range of about 0.1 to 30 MPa, most preferably at a pressure below 5 MPa, with a partial pressure of carbon monoxide advantageously not greater than 50% of the total pressure.

Advantageously, the proportions of carbon monoxide, hydrogen, and ethylene in the feed to the oxo reactor at the foregoing pressures are maintained as follows: CO from about 1 to 50 mol %, preferably about 1 to 35 mol %; $H_2$ from about 1 to 98 mol %, preferably about 10 to 90 mol %; ethylene from about 0.1 to 35 mol %, preferably about 1 to 35 mol %. It will be appreciated that if the dilute ethylene feedstream itself contains significant quantities of carbon monoxide and/or hydrogen, which is not at present preferred, the proportions of syngas and its components may be adjusted accordingly to achieve the desired proportions in the reactor.

The reaction may be conducted either in a batch mode or, preferably, on a continuous basis. In a continuous mode a residence time of up to 4 hours may advantageously be used; if, as indicated as advantageous below, a plurality of reactors is employed, a residence time as short as 1 minute may be employed; otherwise a preferred residence time is in the range of from ½ to 2 hours.

Since the hydroformylation process of the invention advantageously takes place in the liquid phase and the reactants are gaseous compounds, a high contact surface area between the gas and liquid phases is desirable to avoid mass transfer limitations. A high contact surface area between the catalyst solution and the gas phase may be ensured in any suitable manner, for example, by stirring in a batch autoclave operation. In a continuous operation the reactor feed gas can be contacted with the catalyst solution in, for example, a continuous-flow stirred autoclave where the gas is introduced and dispersed at the bottom of the vessel, preferably through a perforated inlet. Good contact between the catalyst and the gas feed may also be ensured by dispersing the solution of the Rh catalyst on a high surface area support, a technique well known in the art as supported liquid phase catalysis, or providing the Rh as part of a permeable gel, although such catalysts may not be commercially preferred.

The hydroformylation reaction may be performed in a single reactor. Suitable reactor schemes are disclosed, for example, in Harris et al in U.S. Pat. Nos. 4,287,369 and 4,287,370 (Davy/UCC), Tsonuda et al in U.S. Pat. No. 4,322,564 (Mitsubishi), Fischer et al in U.S. Pat. No. 4,479, 012, Kummer et al in EP-A-114,611 (both BASF), Cornils et al in EP-A-103,810, Kalbfell et al in EP-A- 144,745 (both Hoechst/Ruhrchemie). optionally two or more reactor vessels or reactor schemes may be configured in parallel. For a dilute feed, a plug flow reactor design, optionally with partial liquid product backmixing, gives a more efficient use of reactor volume than a continuous stirred tank reactor design.

Advantageously, however, hydroformylation is carried out in at least one reaction zone or vessels in series. Suitable reactor configurations are disclosed, for example, by Fowler et al in British Patent Specification No. 1,387,657, by Bunning et al in U.S. Pat. No. 4,593,127, by Miyazawa et al in U.S. Pat. No. 5,105,018, and by Unruh et al in U.S. Pat. No. 5,367,106. In carrying out the present invention with dilute feed gas recycle over one or several reactors is advantageously kept low, or even not used at all. The individual hydroformylation reactors may be of the standard types as described by Denbigh and Turner in "Chemical Reactor Theory" ISBN 0 521 07971 3, by Perry et al in "Chemical Engineers' Handbook" ISBN 0-07-085547-1 or any more recent editions, e.g., a continuous stirred tank or a plug flow reactor with adequate contact of the gas and the liquid flowing through the reactor. Advantageously these plug flow reactor designs or configurations include ways of partial backmixing of the reactor product liquid, as explained, for example, by Elliehausen et al in EP-A-3,985 and in DE 3,220,858).

The presence of diluent in the process of the invention may require different conditions or reactor configurations than are needed for purified ethylene, these differences becoming most important when high conversion of the ethylene is desired. Advantageously, at least 80%, preferably 90% and most preferably 95% of the ethylene in the feedstream is converted. Advantageously high conversions are achieved under reaction conditions which minimize overall reactor size and do not degrade the catalyst. In a single reactor stage, reactor size may be minimized by going to high temperatures (>130° C.); this, however, tends to degrade the catalyst. In a preferred embodiment, therefore, hydroformylation is carried out in different reaction zones. These zones may be different reaction vessels or zones in a single reaction vessel with physically different reaction conditions. An example of a single vessel with different reaction zones is a plug flow reactor in which the temperature increases with travel downstream along the length of the plug flow reactor. By appropriately utilizing different reaction zones, high conversion hydroformylation of ethylene may be achieved with minimum reactor volume and maximum catalyst stability. In a preferred embodiment, two or more reactors are used in series. When two reactors are used they are advantageously staged such that there is an increase in severity (e.g. higher temperatures or catalyst or ligand concentration). Increasing the severity in the second reactor aids in achieving high conversion while minimizing reactor volume and overall catalyst degradation. The reactors used may be two sequential well-stirred tank reactors in which the gaseous dilute ethylene is contacted with a liquid phase that contains the Rh catalyst.

Heat removal from such reactors may be achieved by pumping the liquid or gas phase through a heat exchanger. The gas and liquid in the reactor may be mixed either with an impeller or stirrer or by pumping the gas around through an injector that forms bubbles. In a preferred embodiment the reactors are staged such that more than 70% of the ethylene is converted in the first reactor and more than 70% of the remaining ethylene is converted in the second reactor. This gives an overall ethylene conversion in excess of 91%. Another configuration of two reactors that may be used to obtain high conversion from a dilute ethylene feed is a well-stirred tank reactor followed by a plug flow reactor.

There are several ways of coupling two reactors in series. The simplest is to take the gas phase effluent from the first reactor containing at least unconverted ethylene and propanal vapor and inject it into the second reactor. An alternative scheme is to separate the product propanal between the two reactors by condensing it out of the gas phase material transferring it between the first and second reactors. The composition of the gas exiting the first reactor may be controlled in other ways. For example, some of the hydrogen may be omitted from the feed entering the first reactor and injected into the gas being transferred between the first and second reactor. The liquid phase catalyst solution may or may not be pumped between the two reactors.

The major, and preferred, product of ethylene hydroformylation carried out in accordance with the inventive process is propanal together, possibly, with some propanol. The propanal has utility as an intermediate in the manufacture of numerous commercially important chemicals, and the invention also provides processes in which hydroformylation is followed by reactions producing such chemicals. Where the dilute ethylene feedstream also contains higher unsaturated hydrocarbons, a mixture of aldehydes will result. Such mixtures have especial value when the aldehydes are aldolized, hydrogenated to saturated alcohols, and the alcohols esterified, etherified or formed into acetals to give plasticizers or synthetic lubricants. Under circumstances where the dilute ethylene stream is generated from a low-value feedstock like natural gas, for which in certain areas the cost of transport or the available volume is a major impediment to its commercialization, the products or product mixtures from aldolization and hydrogenation may have value as liquid transportable fuels, optionally after dehydration to the olefin, and if desired hydrogenation to a paraffin or paraffinic mixture.

More especially, the present invention provides a process for the manufacture of propanol, wherein the propanal formed by hydroformylation is hydrogenated; a process for the manufacture of propanoic acid, wherein the propanal is oxidized; a process for the manufacture of an aldol dimer or trimer, wherein the propanal is self-aldolized; a process for the manufacture of a saturated aldehyde, wherein the aldol dimer or trimer is hydrogenated to a corresponding saturated aldehyde; a process for the manufacture of an unsaturated alcohol, wherein the aldol dimer or trimer is selectively hydrogenated; a process for the manufacture of a saturated alcohol, wherein all double bonds in the aldol dimer or trimer are hydrogenated; a process for the manufacture of a saturated alcohol or acid, wherein the saturated aldehyde produced by hydrogenation of the aldol dimer or trimer is hydrogenated or oxidized to form the corresponding saturated alcohol or acid; a process for the manufacture of trimethylol ethane, wherein propanal is condensed with formaldehyde to form the trimethylol ethane; a process for the manufacture of a multi-methylol alkane or alkene, wherein the aldol dimer or trimer and/or the saturated aldehyde produced therefrom is aldol-condensed with formaldehyde to form the corresponding multi-methylol alkane or alkene, a process for the manufacture of an ester, wherein the saturated alcohol or the acid is esterified; a process for the manufacture of an aldol tetramer or pentamer, or mixtures thereof, by aldolization of the propanal or aldehyde mixture from hydroformylation; a process for the manufacture of a $C_{12}$ to $C_{20}$ alcohol or alcohol mixtures, wherein the aldol tetramer, pentamer, or mixture, is hydrogenated to the corresponding alcohol or alcohol mixture; a process for the manufacture of liquid olefin or olefin mixture, wherein the tetramer or pentamer alcohol is dehydrated; and a process for the manufacture of a liquid paraffin or paraffin mixtures, wherein the olefin or olefin mixture is hydrogenated.

One process carried out in accordance with the invention will now be described by way of example only with reference to the accompanying drawings, in which the sole figure is a flow diagram.

BRIEF DESCRIPTION OF THE DRAWING

Referring now to the FIGURE, there is shown a steam cracker (100) producing a process gas (2) containing, inter alia, ethylene from ethane (1). The gas (2) is a feedstream source, which might, for example, have a composition similar to Example A. The gas (2) is processed through a quench step (110) in which water (3) is used to reduce the temperature and stop the reaction. The water removed (4) from this quench contains most of the components, for example $C_5^+$, which are condensable at room temperature and atmopheric pressure. A product stream (5) from the quench is then compressed (120), for example, in several compression stages, to achieve an appropriate pressure, typically from about 0.3 to about 3.8 MPa absolute, for subsequent operations. In the compression, the remainder of the components which are condensable at room temperature ($C_5^+$) and much of the water introduced in the furnace and quench are removed (6) from the dilute ethylene. The dilute ethylene stream (7) is then processed through a caustic wash (130) where a caustic solution (8) is used to remove sulphur- and chlorine-containing components (9). Following caustic wash, water (11) is introduced into the dilute ethylene stream (10) in a water wash (140) to ensure that caustic is not carried forward to the remaining steps and also remove nitrogen-containing compounds (12). The dilute ethylene stream (13), now free of most of the components which act as catalyst poisons in hydroformylation, is then dried using, for example, a molecular sieve (150), with water and any water soluble contaminants or poisons being removed (14). At this point, this dilute ethylene stream (15) is a suitable feedstream to hydroformylation.

Optionally, the stream after drying (15) is further processed to ensure consistency of the non-ethylene unsaturates. The further processing, for example, includes hydrogenation (160) to control the level of acetylene and polyunsaturates. The dilute ethylene (16) is then fractionated (170), with overhead temperatures typically not lower than −50° C., to control the level of $C_4^+$ components which are rejected as heavies (17). Finally, the oxygen level of the dilute ethylene (18) is managed using a fixed bed of reduced metal (180) and, optionally, a fixed bed (190) of additional adsorbent is provided to scavenge, for example, any residual heteroatoms that might remain in the stream (19).

Figure 1:
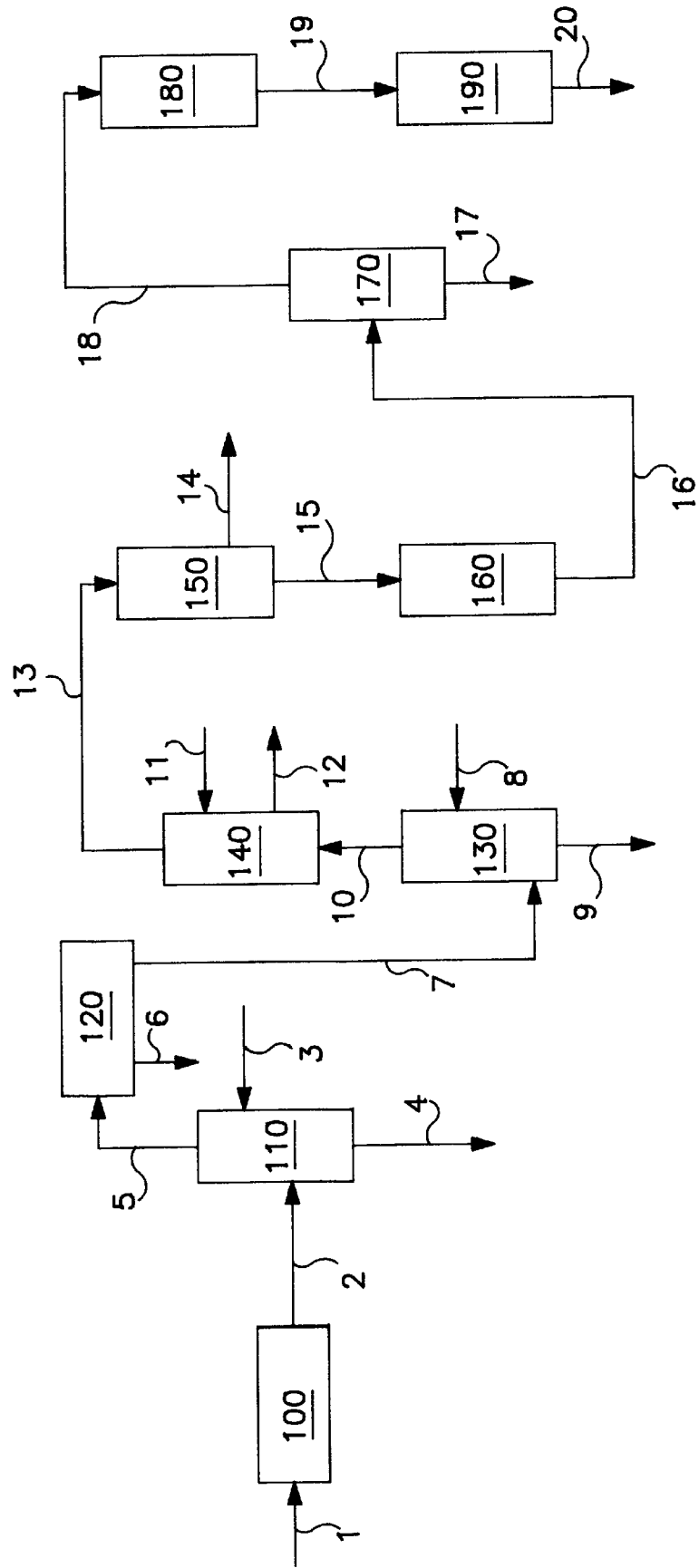

While the process sequence may be altered, for example, drying after hydrogenation for economic or engineering purposes, this processing may produce a dilute ethylene feedstream to hydroformylation (20) with a composition similar to that of Example E above.

The following Examples illustrate the invention.

EXAMPLE 1

This example illustrates continuous hydroformylation of an ethylene/methane mixture. A 500 ml Autoclave Engineering Zipperclave stainless steel autoclave was equipped with a continuous gas feed system, with back pressure control, and with gaseous feed and product characterization via gas chromatography. Catalyst solution was prepared by mixing under nitrogen 201 g of tetraglyme, 15.6 g of triphenylphosphine, and 0.70 mg of rhodium (added as $Rh(CO)_2(acac)$, where acac is the acetylacetonato ligand). This corresponds to 3.23 wppm of Rh, and a P/Rh ratio of 8700. Catalyst solution was tranferred into the autoclave under nitrogen, the autoclave purged with nitrogen, and then gas flows commenced as indicated in Table 1. Pressure then built up to the 1000 kPa (abs) setting of the back pressure control, after which the autoclave and contents were heated to 100° C.

TABLE 1

| Gas Flow Rate (ml/min) | |
|---|---|
| CO | 634 |
| $H_2$ | 688 |
| $CH_4$ | 137 |
| Ethylene | 82 |
| Observed Conversion | 19% |

EXAMPLE 2

The procedures of Example 1 was repeated, but using as catalyst Rh at 85 wppm and a P/Rh ratio of 464, and operating at 90° C. Gas flows and conversion were as shown in Table 2.

TABLE 2

| Gas Flow Rate (ml/min) | |
|---|---|
| CO | 314 |
| $H_2$ | 1776 |
| $CH_4$ | 136 |
| Ethylene | 172 |
| Observed Conversion | 65% |

We claim:

1. A continuous process for the hydroformylation of a dilute ethylene feedstream, said process comprising:
    contacting a dilute ethylene feedstream containing from 27.5 to 75 percent by weight of ethylcne, based on the total hydrocarbon content, and having a total olefin content of at most 80% by weight, based on the total hydrocarbon content, with synthesis gas under hydroformylation conditions in the presence of a rhodium-containing catalyst, wherein said feedstream remains untreated for removal of a compound selected from the group consisting of acetylene, ethane, propane, propene and alkadienes; and
    recovering a hydroformylation product.

2. A process as claimed in claim 1, wherein the feedstream is derived from ethane.

3. A process as claimed in claim 1, wherein the source of the feedstream is the product of a steam cracker.

4. A process as claimed in claim 1, wherein the source of the feedstream to hydrofornylation is compressed, washed with an aqueous alkaline solution and washed with water to form the feedstream.

5. A process as claimed in claim 4, wherein the feedstream is dried to form a dry feedstream.

6. A process as claimed in claim 4, wherein the feedstream or dry feedstrearn is hydrogenated, fractionated, and deoxygenated before hydroformylation.

7. A process as claimed in claim 1, wherein the hydrocarbon content of the feedstream is at least 50% by weight.

8. A process as claimed in claim 7, wherein the hydrocarbon content of the feedstream is at least 80% by weight.

9. A process as claimed in claim 1, wherein the feedstream contains at most 2% by weight of acetylene.

10. A process as claimed in claim 9, wherein the feedstream is substantially free from acetylene.

11. A process as claimed in claim 1, wherein the feedstream contains from 30 to 75% by weight ethylene, based on its total hydrocarbon content.

12. A process as claimed in claim 1, wherein the feedstream contains from 45 to 60% by weight ethylene, based on its total hydrocarbon content.

13. A process as claimed in claim 1, wherein the feedstream contains at most 10% by weight molecular nitrogen.

14. A process as claimed in claim 1, wherein the feedstream contains at most 10 wppm oxygen.

15. A process as claimed in claim 1, wherein the feedstream contains a total of at most 1 wppm sulphur-, chlorine-, and nitrogen-containing compounds.

16. A process as claimed in claim 1, wherein the catalyst is rhodium complexed with carbon monoxide and a triorganophosphorus compound.

17. A process as claimed in claim 16, wherein the compound is triphenylphosphine.

18. A process as claimed in claim 1, wherein the catalyst is in solution.

19. A process as claimed in claim 1, wherein at least 80% of the ethylene in the hydrocarbon-containing feedstream is hydroformylated.

20. A process as claimed in claim 1, wherein hydroformylation is carried out in at least two different reaction zones.

21. A process as claimed in claim 20, wherein the severity of the reaction conditions in at least a second reaction zone is greater than that in a preceding zone.

22. A process as claimed in claim 1, wherein at least 70% of the ethylene is hydroformylated in a first reaction zone and at least 70% of the remaining ethylene is hydroformylated in a second reaction zone.

23. A process as claimed in claim 1, wherein hydroformylation is carried out in at least two separate reactors.

24. A process as claimed in claim 23, wherein at least one reactor operates as a stirred tank reactor and at least one reactor operates in plug flow mode.

25. A process as claimed in claim 23, wherein there are used at least two stirred tank reactors, within which the catalyst is in a liquid phase and ethylene is in a gaseous phase.

26. A process as claimed in claim 1, wherein the hydroformylation product is propanal.

27. A process as claimed in claim 26, wherein the propanal is hydrogenated to propanol.

28. A process as claimed in claim 26, wherein the propanal is oxidized to propanoic acid.

29. A process as claimed in claim 26, wherein the propanal is subsequently aldolized.

30. A process as claimed in claim 26, wherein the propanal is condensed with formaldehyde to form trimethylolethane.

31. A process as claimed in claim 26, wherein the propanal is subjected to aldolization to form an unsaturated dimer, trimer, tetramer or pentamer.

32. A process as claimed in claim 31, wherein the unsaturated product is hydrogenated to form a saturated aldehyde, or an unsaturated or saturated alcohol.

33. A process as claimed in claim 32, wherein a saturated alcohol is formed, and the saturated product is dehydrated to form an olefin.

34. A process as claimed in claim 33, wherein the olefin is hydrogenated to form an alkane.

35. A process as claimed in claim 31, wherein the unsaturated product is converted, via a saturated aldehyde, to an acid.

36. A process as claimed in claim 31, wherein the unsaturated product or a saturated aldehyde produced therefrom is condensed with formaldehyde to a corresponding multimethylol alkane or alkene.

37. A process for the manufacture of an ester, which comprises esterifying an alcohol produced by a process as claimed in claim 32.

38. A process for the manufacture of an ester, which comprises esterifying an acid produced by a process as claimed in claim 35.

* * * * *